United States Patent [19]

Knowles

[11] Patent Number: 5,514,817
[45] Date of Patent: May 7, 1996

[54] SUBSTITUTED PHENANTHROPYRANS

[75] Inventor: David B. Knowles, Apollo, Pa.

[73] Assignee: PPG Industries, Inc., Pittsburgh, Pa.

[21] Appl. No.: 286,039

[22] Filed: Aug. 4, 1994

[51] Int. Cl.$^6$ .................. C07D 311/78; C07D 311/96; G02B 5/23; C08K 5/15
[52] U.S. Cl. .................. 549/384; 549/331; 549/60; 549/58; 548/525; 546/269; 546/256; 546/196; 524/110; 252/586
[58] Field of Search .................. 549/384, 331, 549/58, 60; 252/586; 524/110; 548/525; 546/269, 256, 196

[56] References Cited

U.S. PATENT DOCUMENTS

| | | | |
|---|---|---|---|
| 3,567,605 | 3/1971 | Becker | 204/158 |
| 3,627,690 | 12/1971 | Casella et al. | 252/300 |
| 4,342,668 | 8/1982 | Hovey et al. | 252/586 |
| 4,637,698 | 1/1987 | Kwak et al. | 351/163 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/160 |
| 4,980,009 | 12/1990 | Heller | 252/586 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |
| 5,340,857 | 8/1994 | Van Gemert | 524/110 |

FOREIGN PATENT DOCUMENTS

| | | |
|---|---|---|
| 7-41758 | 2/1995 | Japan . |
| 7-48363 | 2/1995 | Japan . |
| 7-48566 | 2/1995 | Japan . |
| 7-48567 | 2/1995 | Japan . |

OTHER PUBLICATIONS

*Friedel–Crafts and Related Reactions*, George A. Olah, Interscience Publishers, vol. 3, Chap. XXXI, pp. 1–8, 1964.
"Regioselective Friedel Crafts Acylation of 1,2,3,4—Tetrahydroquinoline and Related Nitrogen Heterocycles: Effects of NH Protective Groups and Ring Size", Ishihara, Y., et al, J. Chem. Soc., Perkin Trans. 1, pp. 3401–3406, 1992.
Organic Reactions, vol. VI, John Wiley and Sons, Inc. Chapter 1, pp. 1–2 (1951).
*Organic Reactions*, vol. 9, John Wiley and sons, Inc. pp. 37–72 (1957).
*Research Disclosure*, No. 36144, pp. 267 and 268, May, 1994.

Primary Examiner—Nicky Chan
Attorney, Agent, or Firm—Frank P. Mallak; Irwin M. Stein

[57] ABSTRACT

Described are novel reversible photochromic phenanthropyran compounds, examples of which are substituted 2H-phenanthro[4,3-b]pyran and 3H-phenanthro[1,2-b]pyran compounds. The 2H-phenanthropyran compounds have certain substituents at the number 5 and 6 carbon atoms of the phenanthro portion of the phenanthropyran and at the 2 position of the pyran ring. Certain substituents may also be present at the number 7, 8, 9, 10, 11, or 12 carbon atoms of the phenanthro portion of the phenanthropyran. The 3H-phenanthropyran compounds have certain substituents at the number 11 and 12 carbon atoms of the phenanthro portion of the phenanthropyran and at the 3 position of the pyran ring. Certain substituents may also be present at the number 5, 6, 7, 8, 9, or 10 carbon atoms of the phenanthro portion of the phenanthropyran. Also described are polymeric organic host materials that contain or that are coated with such compounds. Articles such as ophthalmic lenses or other plastic transparencies that incorporate the novel phenanthropyran compounds or combinations thereof with complimentary photochromic compounds, e.g., spiro(indoline)type compounds, chromenes, and certain benzopyrans, are also described.

20 Claims, No Drawings

SUBSTITUTED PHENANTHROPYRANS

DESCRIPTION OF THE INVENTION

The present invention relates to certain novel phenanthropyran compounds. More particularly, this invention relates to novel photochromic phenanthropyran compounds and to compositions and articles containing such novel phenanthropyran compounds. When exposed to light radiation involving ultraviolet rays, such as the ultraviolet radiation in sunlight or the light of a mercury lamp, many photochromic compounds become activated, i.e., change light transmission properties, and exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. U.S. Pat. No. 3,627,690 describes photochromic 2,2-di-substituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses.

The present invention relates to novel substituted photochromic 2H-phenanthro[4,3-b]pyran and 3H-phenanthro[1,2-b]pyran compounds. The 2H-phenanthropyran compounds have certain substituents at the number 5 and 6 carbon atoms of the phenanthro portion of the phenanthropyran and at the 2 position of the pyran ring. Certain substituents may also be present at the number 7, 8, 9, 10, 11, or 12 carbon atoms of the phenanthro portion of the phenanthropyran. The 3H-phenanthropyran compounds have certain substituents at the number 11 and 12 carbon atoms of the phenanthro portion of the phenanthropyran and at the 3 position of the pyran ring. Certain substituents may also be present at the number 5, 6, 7, 8, 9, or 10 carbon atoms of the phenanthro portion of the phenanthropyran.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

Photochromic compounds that are most useful in optical applications, such as conventional ophthalmic lenses, are those which possess (a) a high quantum efficiency for coloring in the near ultraviolet, (b) a low quantum yield for bleaching with white light, and (c) a relatively fast thermal fade at ambient temperature but not so rapid a thermal fade rate that the combination of white light bleaching and thermal fade prevent coloring by the ultraviolet component of strong sunlight. In addition, the aforesaid properties are desirably retained in conventional rigid synthetic plastic materials customarily used for ophthalmic and plano lenses when such materials have applied to or incorporated therein such photochromic compounds.

In accordance with the present invention, it has now been discovered that certain novel photochromic phenanthropyran compounds may be prepared. These compounds may be described as 2H-phenanthro[4,3-b]pyrans having certain substituents at the number 5 and 6 carbon atoms of the phenanthro portion and at the 2 position of the pyran ring, and as 3H-phenanthro[1,2-b]pyran having certain substituents at the number 11 and 12 carbon atoms of the phenanthro portion and at the 3 position of the pyran ring. Certain substituents may also be present on the 2H-phenanthropyran at the number 7, 8, 9, 10, 11, or 12 carbon atoms, and on the 3H-phenanthropyran at the number 5, 6, 7, 8, 9, or 10 carbon atoms of the phenanthro portion of the phenanthropyran. The 2H-phenanthropyrans and the 3H-phenanthropyrans are represented by the following graphic formulae I A and I B, respectively:

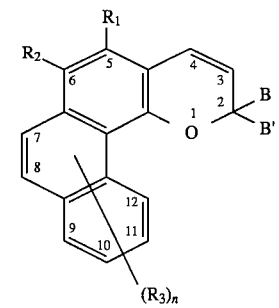

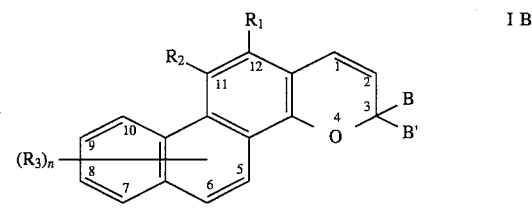

In graphic formulae I A and I B, $R_1$ is the group, $CH_2X$ or $-C(O)Y$, wherein X is hydroxy, benzoyloxy, $C_1$–$C_6$ alkoxy, e.g., methoxy, ethoxy, propoxy, butoxy, etc., $C_1$–$C_6$ acyloxy, e.g., acetoxy and propionyloxy, $C_2$–$C_6$ dialkylamino, e.g., dimethylamino and diethylamino, or trimethylsilyloxy, Y is the group, $-OR_4$ or $-N(R_5)R_6$, wherein $R_4$ is hydrogen, $C_1$–$C_6$ alkyl, e.g., methyl, ethyl, propyl, butyl, pentyl, and hexyl, phenyl, mono($C_1$–$C_6$)alkyl substituted phenyl, mono($C_1$–$C_6$)alkoxy substituted phenyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl, or $C_1$–$C_6$ haloalkyl; and $R_5$ and $R_6$ may each be selected from the group consisting of hydrogen, $C_1$–$C_6$ alkyl, $C_5$–$C_7$ cycloalkyl, phenyl, mono-substituted phenyl, and di-substituted phenyl, or $R_5$ and $R_6$ together with the nitrogen may form an unsubstituted, mono-substituted or di-substituted heterocyclic ring containing from 5 to 6 ring atoms, which heterocyclic ring has said nitrogen as the sole hetero atom or has said nitrogen atom and one additional atom of nitrogen or oxygen as hetero atoms. The phenyl and heterocyclic ring substituent may be $C_1$–$C_6$ alkyl or $C_1$–$C_6$ alkoxy and the halo substituent may be chloro or fluoro.

$R_2$ in graphic formulae IA and IB may be hydrogen, $C_1$–$C_6$ alkyl, $C_3$–$C_7$ cycloalkyl, 2-, 3-, or 4-pyridyl, i.e., 2-pyridyl, 3-pyridyl, or 4-pyridyl, phenyl, or mono- or di-substituted phenyl. The phenyl substituents may be $C_1$–$C_6$ alkyl, $C_1$–$C_6$ alkoxy, chloro, or fluoro. In graphic formulae IA and IB, each $R_3$ may be chloro, fluoro, amino, $C_1$–$C_6$ monoalkylamino, $C_2$–$C_6$ dialkylamino, $C_1$–$C_6$ alkyl or —$OR_7$, wherein $R_7$ is hydrogen, $C_1$–$C_6$ alkyl, allyl, or acetyl, and n is selected from the integers 0, 1, or 2.

B and B' in graphic formulae I A or I B may each be selected from the group consisting of: (i) the unsubstituted, and the mono-, di-, or tri-substituted aryl groups phenyl and naphthyl, e.g., 1- or 2-naphthyl; (ii) the substituted or unsubstituted heterocyclic aromatic groups 2-, 3-, or 4-pyridyl, 2- or 3-furanyl, 2- or 3-benzofuranyl, 2- or 3-thienyl, and 2- or 3-benzothienyl, said aryl and heterocyclic substituents being selected from the group consisting of hydroxy, amino, $C_1$–$C_6$ monoalkylamino, $C_2$–$C_6$ dialkylamino, $C_1$–$C_6$ alkyl, $C_1$–$C_6$ haloalkyl, $C_1$–$C_6$ alkoxy, mono($C_1$–$C_6$)alkoxy($C_1$–$C_4$)alkyl, acryloxy, methacryloxy, and halogen, said halogen or (halo) group being fluoro or chloro; (iii) the groups represented by the following graphic formulae II A and II B:

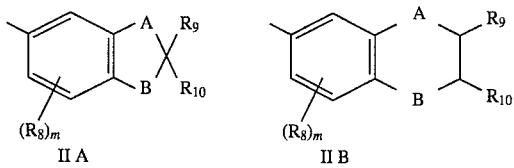

wherein A may be carbon or oxygen and B may be oxygen or substituted nitrogen, provided that when B is substituted nitrogen, A is carbon, and the nitrogen substituents may be selected from the group consisting of hydrogen, $C_1$–$C_6$ alkyl, and $C_2$–$C_6$ acyl. Each $R_8$ in graphic formulae II A and II B may be $C_1$–$C_6$ alkyl, $C_1$–$C_6$ alkoxy, hydroxy, or halogen, said halogen being chloro or fluoro; $R_9$ and $R_{10}$ may each be hydrogen or $C_1$–$C_6$ alkyl and m is the integer 0, 1, or 2; and (iv) $C_1$–$C_6$ alkyl, $C_1$–$C_6$ haloalkyl, $C_1$–$C_6$ alkoxy($C_1$–$C_4$)alkyl, $C_3$–$C_6$ cycloalkyl, mono ($C_1$–$C_6$) alkoxy ($C_3$–$C_6$) cycloalkyl, mono ($C_1$–$C_6$) alkyl ($C_3$–$C_6$) cycloalkyl, and halo ($C_3$–$C_6$) cycloalkyl, said halo group being fluoro or chloro; or (v) B and B' taken together may form substituted or unsubstituted fluoren-9-ylidene or the substituted or unsubstituted, saturated bicyclic ring compound selected from the group consisting of adamantylidene, bornylidene, norbornylidene, and bicyclo(3.3.1)nonan-9-ylidine.

More preferably, the 2H-phenanthropyran and 3H-phenanthropyran compounds of the present invention are represented by the following graphic formulae III A and III B, respectively:

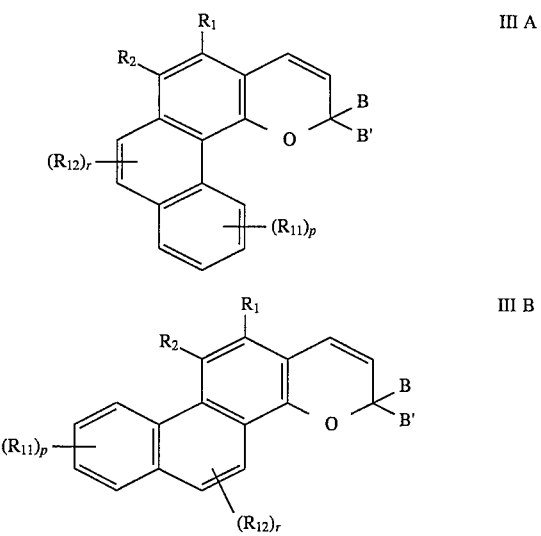

In graphic formulae III A and III B, $R_1$ is the group —$CH_2X$ or —C(O)Y, wherein X may be hydroxy, $C_1$–$C_4$ alkoxy, $C_1$–$C_4$ acyloxy, or $C_2$–$C_4$ dialkylamino, Y is the group, —$OR_4$ or —$N(R_5)R_6$, wherein $R_4$ may be hydrogen, $C_1$–$C_4$ alkyl, phenyl, mono($C_1$–$C_4$)alkyl substituted phenyl, mono($C_1$–$C_4$)alkoxy substituted phenyl, phenyl($C_1$–$C_2$)alkyl, mono($C_1$–$C_4$) alkyl substituted phenyl($C_1$–$C_2$)alkyl, mono($C_1$–$C_4$)alkoxy substituted phenyl($C_1$–$C_2$)alkyl, $C_1$–$C_4$ alkoxy($C_2$–$C_3$)alkyl, or $C_1$–$C_4$ haloalkyl, and $R_5$ and $R_6$ may each be selected from the group consisting of hydrogen, $C_1$–$C_4$ alkyl, $C_5$–$C_6$ cycloalkyl, phenyl, mono-substituted phenyl, and di-substituted phenyl. The phenyl substituents may be $C_1$–$C_4$ alkyl or $C_1$–$C_4$ alkoxy and the halo substituent may be chloro or fluoro. Preferably, $R_1$ is the group —$CH_2X$ or —C(O)Y, wherein X may be hydroxy, $C_1$–$C_3$ alkoxy, or $C_1$–$C_3$ acyloxy, Y is the group —$OR_4$ or —$N(R_5)R_6$, wherein $R_4$ may be hydrogen, $C_1$–$C_3$ alkyl, or phenyl; and $R_5$ and $R_6$ may each be hydrogen or $C_1$–$C_3$ alkyl.

$R_2$ in graphic formulae III A and III B may be hydrogen, $C_1$–$C_4$ alkyl, $C_3$–$C_5$ cycloalkyl, phenyl, or monosubstituted or di-substituted phenyl. The phenyl substituents may be $C_1$–$C_4$ alkyl, $C_1$–$C_4$ alkoxy, chloro, or fluoro. Preferably, $R_2$ is hydrogen, $C_1$–$C_3$ alkyl, phenyl, or monosubstituted phenyl. The preferred phenyl substituents are $C_1$–$C_2$ alkyl, $C_1$–$C_2$ alkoxy, or fluoro.

In graphic formulae III A and III B, each $R_{11}$ and each $R_{12}$ may be chloro, fluoro, amino, $C_1$–$C_6$ monoalkylamino, $C_2$–$C_6$ dialkylamino, $C_1$–$C_4$ alkyl, or the group, —$OR_7$, wherein $R_7$ may be hydrogen, $C_1$–$C_4$ alkyl, or acetyl; and p and r are each the integers 0 or 1. Preferably, each $R_{11}$ and each $R_{12}$ are $C_1$–$C_3$ alkyl or —$OR_7$, wherein $R_7$ is hydrogen, $C_1$–$C_3$ alkyl, or acetyl.

B and B' in graphic formulae III A and III B, are each selected from the group consisting of: (i) phenyl, monosubstituted phenyl, or di-substituted phenyl, said phenyl substituents being selected from the group consisting of $C_1$–$C_3$ alkyl, $C_1$–$C_3$ alkoxy, amino, $C_1$–$C_4$ monoalkylamino, $C_2$–$C_4$ dialkylamino, and fluoro; (ii) the groups represented by graphic formulae II A and II B, wherein A is carbon and B is oxygen, $R_8$ is $C_1$–$C_3$ alkyl or $C_1$–$C_3$ alkoxy, and $R_9$ and $R_{10}$ are each hydrogen or $C_1$–$C_4$ alkyl, and m is the integer 0 or 1; and (iii) $C_1$–$C_4$ alkyl; or (iv) B and B' taken together form substituted or unsubstituted fluoren-9-ylidene or adamantylidene. Still more preferably, the phenyl substituents are in the ortho and/or para position(s).

Compounds represented by graphic formulae I A, I B, III A, and III B may be prepared by the following reactions A through G. Compounds represented by graphic formula VI or VI A are either purchased or prepared by the Friedel-Crafts methods shown in reaction A using an appropriately substituted or unsubstituted benzoyl chloride of graphic formula V with a commercially available substituted or unsubstituted benzene compound of graphic formula IV. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In reaction A, the compounds represented by graphic formulae IV and V are dissolved in a solvent, such as carbon disulfide or methylene chloride, and reacted in the presence of a Lewis acid, such as aluminum chloride or tin tetrachloride, to form the corresponding substituted ketone represented by graphic formula VI (or VIA in reaction B). R and R' represent potential phenyl substituents.

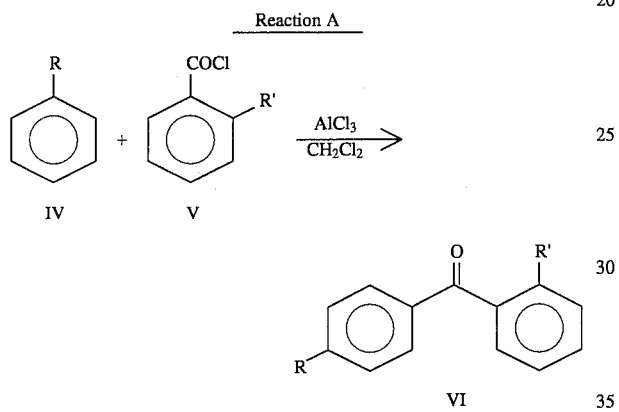

In reaction B, the substituted or unsubstituted ketone represented by graphic formula VI A (in which B and B' may represent groups other than substituted or unsubstituted phenyl) is reacted with sodium acetylide in a suitable solvent, such as anhydrous tetrahydrofuran, to form the corresponding propargyl alcohol represented by graphic formula VII. Propargyl alcohols having B or B' groups other than substituted and unsubstituted phenyl may be prepared from commercially available ketones or via reaction of an acyl halide with a substituted or unsubstituted benzene, naphthalene, or heteroaromatic compound.

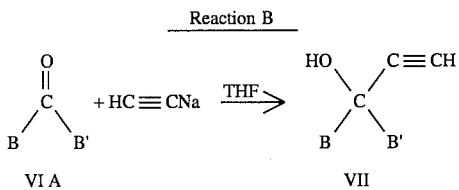

Starting materials such as an appropriately substituted acetonaphthone or naphthaldehyde for use in the Stobbe condensation shown in Reaction D and E, represented by graphic formulae XI and XVI, respectively, may be available commercially or custom synthesized. For example, acetonaphthones may be prepared by Friedel-Crafts methods as shown in Reaction C where 1-methoxynaphthalene represented by graphic formula VIII and a commercially available acyl or aroyl chloride represented by graphic formula IX are dissolved in a solvent such as methylene chloride or carbon disulfide and reacted in the presence of a Lewis acid such as aluminum chloride or tin tetrachloride to form the substituted acetonaphthone represented by graphic formula X. See the publication, *Friedel-Crafts and Related Reaction*, George A. Olah, Interscience Publishers, 1964, Vol. 3 Chapter XXXI (Aromatic Ketone Synthesis). Substituted naphthaldehydes may also be prepared by a variety of methods such as the Garterman reaction. For a review see Truce, Organic Reactions, Volume 9, pages 37 to 72, 1957.

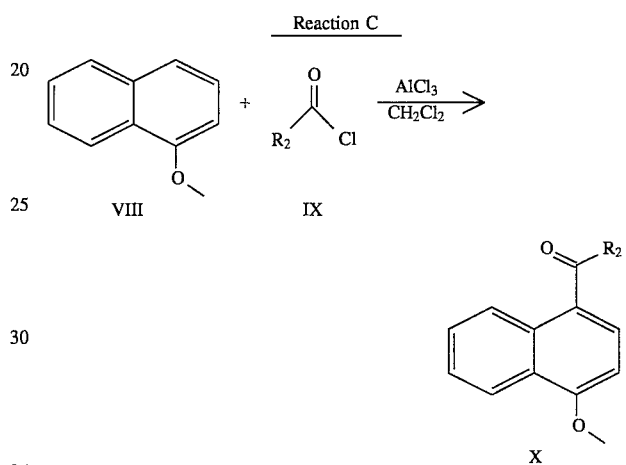

An appropriate substituted acetonaphthone or naphthaldehyde represented by graphic formulae XI or XVI in Reaction D and E, respectively, is reacted with an ester of a succinic acid such as dimethyl succinate represented by graphic formula XII. A solvent, such as toluene, containing either sodium hydride or potassium t-butoxide as the base, to which the reactants are added yields a mixture of cis and trans alkylidenesuccinic acids or half-esters represented by graphic formulae XIII or XVII. Alkylidenesuccinic acids or half-esters having the correct stereochemical configuration undergo cyclodehydration and enolization in the presence of acetic anhydride and sodium acetate to form phenanthroates whose general structure is represented by graphic formulae XIV or XVIII. Alcoholysis then yields a substituted 1-hydroxy-3-methoxycarbonylphenanthrene or 4-hydroxy-2methoxycarbonylphenanthrene represented by graphic formulae XV or XIX, respectively. Many known examples of the Stobbe condensation and cyclization may be found in the literature. See the publication, The Stobbe Condensation, William S. Johnson and Guido H. Daub, John Wiley and Sons, Inc., Organic Reactions, Volume VI, pages 1 to 73, 1951.

Reaction D
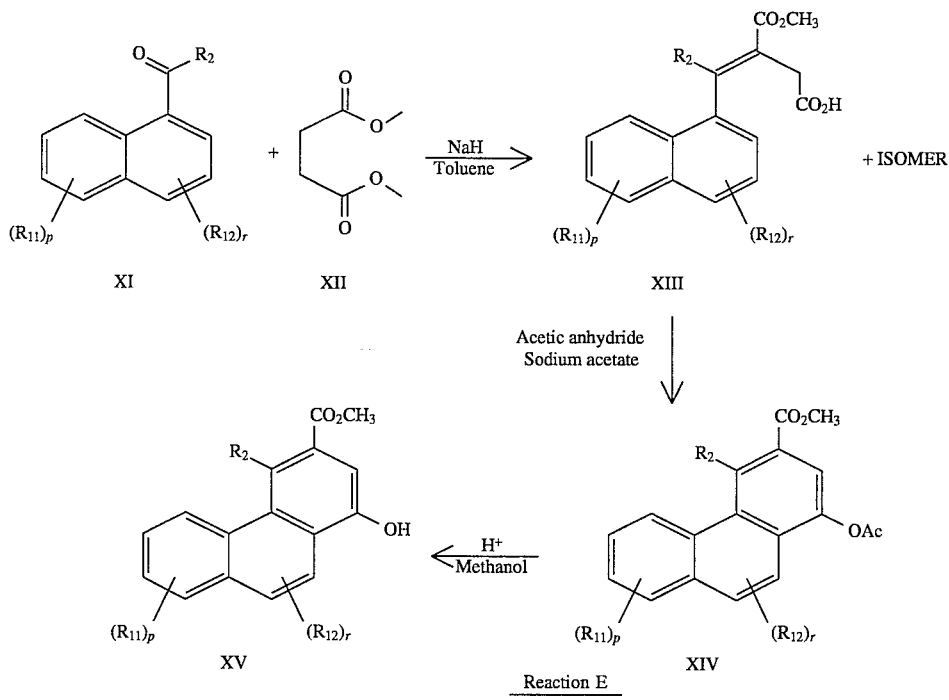
Reaction E
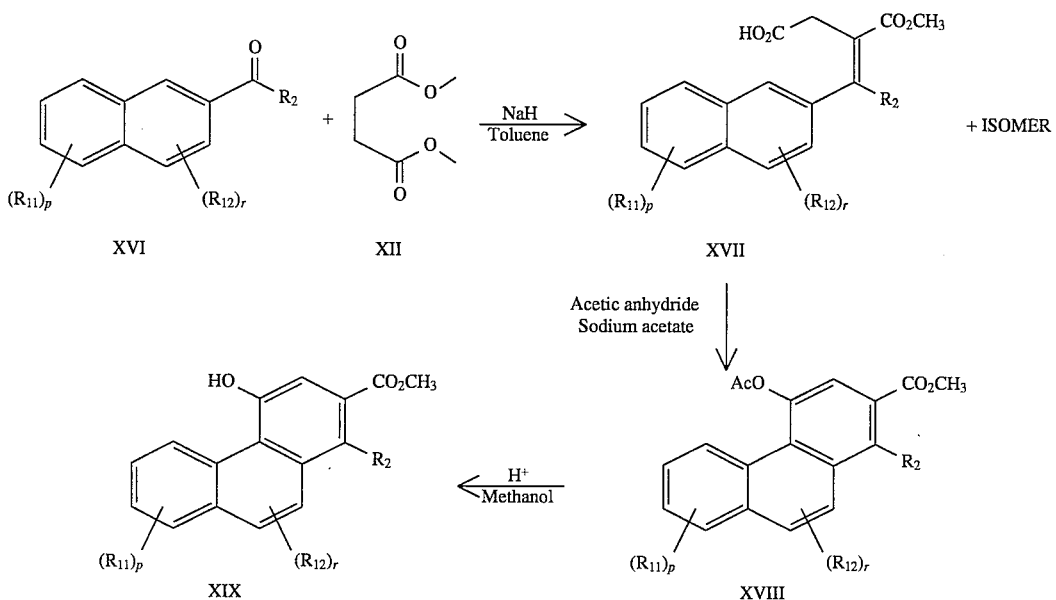
In Reaction F, either of the substituted phenanthrols represented by graphic formulae XX or XXI can be coupled with an appropriately substituted propargyl alcohol represented by graphic formula VII to produce compounds represented by graphic formulae III A 1 or III B 1.

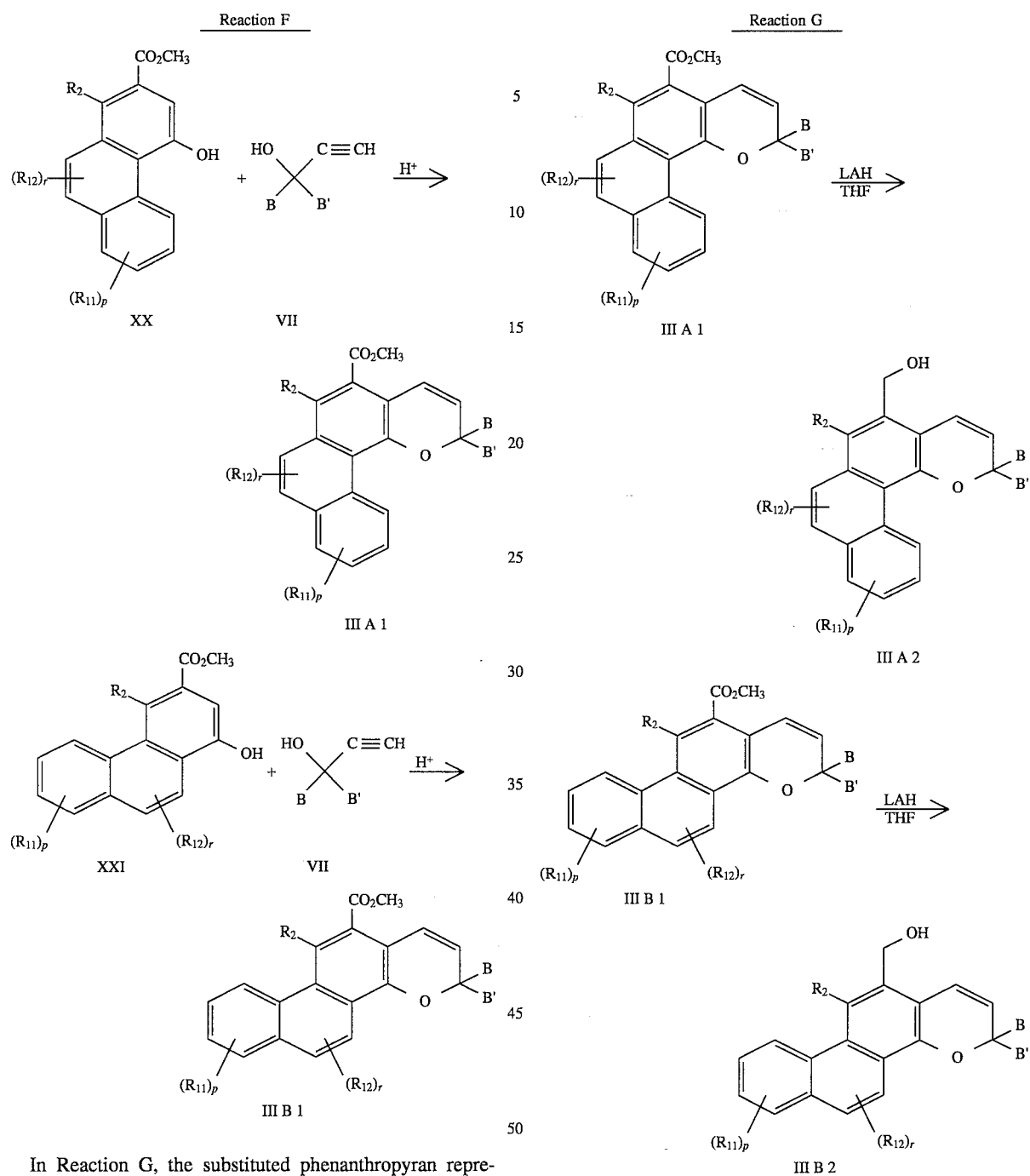

In Reaction G, the substituted phenanthropyran represented by graphic formulae III A 1 or III B 1 is dissolved in a suitable solvent such as tetrahydrofuran. Lithium aluminum hydride is added to reduce the methoxycarbonyl group to a hydroxy methylene group in the resulting compounds represented by graphic formula III A 2 and III B 2, respectively.

Compounds represented by graphic formulae I A, I B, the III A series, i.e., III A, III A 1, and III A 2, and the III B series may be used in those applications in which organic photochromic substances may be employed, such as optical lenses, e.g., vision correcting ophthalmic and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Phenanthropyrans represented by graphic formulae I A, I B, the III A series, and the III B series exhibit color changes from colorless to colors ranging from yellow to purple.

Examples of contemplated phenanthropyrans within the scope of the invention are the following:
(a) 3,3-diphenyl-12-methoxycarbonyl-11-methyl-3H-phenanthro[1,2-b]pyran;
(b) 2,2-diphenyl-5-methoxycarbonyl-6-methyl-2H-phenanthro[4,3-b]pyran;
(c) 2-(4-methoxyphenyl)-2-phenyl-5-methoxycarbonyl-6-methyl-2H-phenanthro[4,3-b]pyran;
(d) 3-(2-fluorophenyl)-3-(4-methoxyphenyl)-6-methoxy-12-methoxycarbonyl-12-methoxycarbonyl-3 H-phenanthro[1,2-b]pyran;
(e) spiro [3H-6-methoxy-12-methoxycarbonylphenanthro[1,2-b]pyran-3-9'-fluorene];
(f) 2,2-di(4-methoxyphenyl)-10-methoxy-5-methoxycarbonyl-6-methyl-2H-phenanthro[4,3-b]pyran;
(g) 3-(2,3-dihydrobenzofur-5-yl)-3-(4-methoxyphenyl)-6-methoxy-12-methoxycarbonyl-11-methyl -3H-phenanthro[1,2-b]pyran;
(h) 3,3-diphenyl-6-methoxy-12-methoxycarbonyl-11-phenyl-3H-phenanthro[1,2-b]pyran;
(i) 3-(4-methoxyphenyl)-3-(2-methyl-2,3-dihydrobenzofur-5-yl)-6-methoxy-12-methoxycarbonyl -11-phenyl-3H-phenanthro[1,2-b]pyran;
(j) 3-(4-methoxyphenyl)-3-(2-methyl-2,3-dihydrobenzofur-5-yl)-6-methoxy-12-hydroxymethyl -11-phenyl-3H-phenanthro[1,2-b]pyran; and
(k) 2,2-diphenyl-5-N,N-dimethylaminocarbonyl-2H-phenanthro[4,3-b]pyran.

Commercially available photoreactive inorganic glass lenses containing silver halide particles darken to a neutral gray or brown color in sunlight. In order to duplicate this color change in a plastic lens using the organic photochromic phenanthropyrans of the present invention, it is contemplated that such phenanthropyrans be used alone or in combination with other appropriate complimentary organic photochromic materials to produce the desired gray or brown color shade when the plastic lens containing such photochromic materials is exposed to ultraviolet light. For example, a single phenanthropyran compound having two visible absorption peaks, i.e., one that produces a yellow color and the other a purple color, yields an appropriate brown shade when used by itself. Similarly, a phenanthropyran compound having two visible absorption peaks that individually produce orange and blue colors yields an appropriate gray shade without the addition of other photochromic compounds or dyes. Alternatively, combinations of phenanthropyran compounds of the present invention with other organic photochromic materials having one, two, or more complimentary visible absorption peaks that produce appropriate colors may be used.

The novel substituted 2H-phenanthro[4,3-b]pyran and 3H-phenanthro[1,2-b]pyran compounds of the present invention, such as those heretofore described, may be used alone or in combination with complimentary photochromic compounds, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

A first group of complimentary organic photochromic substances contemplated for use to prepare photochromic articles of the present invention are those having an activated absorption maximum within the visible range of greater than 590 nanometers, e.g., between about greater than 590 to 700 nanometers. These materials typically exhibit a blue, blueish-green, or blueish-purple color when exposed to ultraviolet light in an appropriate solvent or matrix. Many of such compounds are described in the open literature. For example, spiro(indoline)naphthoxazines have been described, among others, in U.S. Pat. Nos. 3,562,172; 3,578,602; 4,215,010; and 4,342,668. Spiro(indoline)naphthoxazines having certain substituents on the 8' and 9' positions of the naphthoxazine portion of the molecule are the subject of copending U.S. patent application Ser. No. 07/993,587, filed Dec. 21, 1992. Spiro(indoline)pyridobenzoxazines are described in U.S. Pat. No. 4,637,698. Spiro(benzindoline)pyridobenzoxazines and spiro(benzindoline)naphthoxazines are described in U.S. Pat. No. 4,931,219. Spiro(benzindoline)naphthopyrans are described in Japanese Patent Publication 62/195383. Spiro(indoline)benzoxazines are described in U.S. Pat. No. 4,816,584. Spiro(indoline)benzopyrans, spiro(indoline)naphthopyrans and spiro(indoline)quinopyrans are described, for example, in U.S. Pat. No. 4,880,667. Benzopyrans and naphthopyrans having a nitrogen-containing substituent in the 2-position of the pyran ring are described in U.S. Pat. No. 4,818,096. Spiro(indoline)pyrans are also described in the text, *Techniques in Chemistry*, Volume III, "Photochromism," Chapter 3, Glenn H. Brown, Editor, John Wiley and Sons, Inc., New York, 1971.

A second group of complimentary organic photochromic substances contemplated for use to prepare photochromic articles of the present invention are those having at least one absorption maximum and preferably two absorption maxima, within the visible range of between about 400 and less than 500 nanometers. These materials typically exhibit a yellow-orange color when exposed to ultraviolet light in an appropriate solvent or matrix. Such compounds include certain chromenes, i.e., benzopyrans and naphthopyrans. Many of such chromenes are described in the open literature, e.g., U.S. Pat. Nos. 3,567,605; 4,826,977; and 5,066,818. Examples of benzopyrans and naphthopyrans having a spiro adamantane group at the 2-position of the naphthopyran ring are described in U.S. Pat. No. 4,826,977. Naphthopyrans having at least one ortho-substituted phenyl substituent at the 3-position of the pyran ring are described in U.S. Patent 5,066,818. Naphthopyran compounds having certain substituents at the number 8 carbon atom and certain substituents at the number 7 or 9 carbon atom, all substituents being on the naphtho portion of the naphthopyran, are the subject of co-pending U.S. patent application Ser. No. 08/080,246, filed Jun. 21, 1993. Naphthopyrans substituted at the 3 position of the pyran ring with (i) an aryl substituent and (ii) a phenyl substituent having a 5- or 6-member heterocyclic ring fused at the number 3 and 4 carbon atoms of the phenyl substituent are the subject of co-pending U.S. patent application Ser. No. 08/080,250 filed Jun. 21, 1993. Naphthopyran compounds substituted at the number 8 carbon atom on the naphtho portion of the naphthopyran ring, with for example, a methoxy group are the subject of U.S. Pat. No. 5,238,931. Naphthopyran compounds, examples of which are 3-aryl-3-arylalkenyl naphthopyrans, are described in U.S. Pat. No. 5,274,132.

A third group of complimentary organic photochromic substances contemplated for use to form the photochromic articles of the present invention are those having an absorption maximum within the visible range of between about 400 to about 500 nanometers and another absorption maximum within the visible range of between about 500 to about 700 nanometers. These materials typically exhibit color(s) ranging from yellow/brown to purple/gray when exposed to ultraviolet light in an appropriate solvent or matrix. Examples of these compounds include certain benzopyran compounds, such as those having substituents at the 2-position of the pyran ring and a substituted or unsubstituted heterocyclic ring, such as a benzothieno or benzofurano ring fused to the benz portion of the benzopyran. Such materials are the subject of co-pending U.S. patent application No. 08/201,948, filed Feb. 24, 1994.

The disclosures of such photochromic compounds in the aforedescribed patents and patent applications are incorporated herein, in toro, by reference. The photochromic articles of the present invention may contain one photochromic compound or a mixture of photochromic compounds, as desired. Individual photochromic compounds or mixtures of photochromic compounds may be used to attain certain activated colors such as a near neutral gray or brown.

The novel phenanthropyrans of the present invention exhibit activated colors of from yellow to purple, and therefore may be used in place of or in combination with the aforesaid third group of photochromic compounds. The compounds of the present invention (hereinafter also referred to and included as a third group photochromic compound) may be used alone or in combination with the organic photochromic substances of the second complimentary group described herein, i.e., those that color to yellow/orange and/or with the organic photochromic substances of the first complimentary group that color to purple/blue, e.g., the spirooxazine-type compounds. Each of the photochromic substances described herein may be used in amounts and in a ratio such that an organic host material to which the mixture of compounds is applied or in which they are incorporated exhibits a desired resultant color, e.g., a substantially neutral color such as shades of gray or brown, when activated with unfiltered sunlight, i.e., as near a neutral color as possible given the colors of the activated photochromic compounds. The relative amounts of the aforesaid photochromic compounds used will vary and depend in part upon the relative intensities of the color of the activated species of such compounds, and the ultimate color desired. Generally, the weight ratio of the aforedescribed organic photochromic substance combination, i.e., (first to third) and (second to third), will vary from about 1:3 to about 3:1, e.g., between about 0.75:1 and about 2:1. The combination of the first, second, and third described organic photochromic substances may have a weight ratio that will vary from about 1:3:1 to 3:1:3.

A near neutral gray color exhibits a spectrum that has relatively equal absorption in the visible range between 400 and 700 nanometers, e.g., between 440 and 660 nanometers. A near neutral brown color exhibits a spectrum in which the absorption in the 440–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used in the specification, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The photochromic substances of the present invention may be applied to or incorporated into a host material by various methods described in the art. Such methods include dissolving or dispersing the substance within the host material, e.g., casting in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The polymeric organic host material will usually be transparent, but may be translucent or even opaque. The polymeric product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the polymer color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. No. 4,360,653 and 4,994,208; and copolymers with aliphatic urethanes, the terminal portion of which contain allyl or acrylyl functional groups as described in U.S. Pat. No. 5,200,485; cellulose acetate, cellulose propionate, cellulose butyrate, cellulose acetate butyrate, polystyrene and copolymers of styrene with methyl methacrylate, vinyl acetate and acrylonitrile.

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity. Generally, the amount of total photochromic substance incorporated into or applied to a photochromic optical host material may range from about 0.15 to about 0.35 milligrams per square centimeter of surface to which the photochromic substance(s) is incorporated or applied.

The present invention is more particularly described in the following examples which are intended as illustrative only, since numerous modifications and variations therein will be apparent to those skilled in the art.

EXAMPLE 1

STEP 1

1'-Acetonaphthone (20.0 grams, 0.12 mole) and dimethyl succinate (19.0 grams, 0.13 mole) were mixed together and 20 weight percent of the reagent mixture was added to a reaction flask containing 200 milliliters (mL) of anhydrous toluene and sodium hydride (7.2 grams of a 60 weight percent suspension in mineral oil, 0.18 mole). The reaction flask had a large head space because the reaction is highly exothermic and excessively foamy due to the rapid evolution of hydrogen gas. One mL of methanol was added to the reaction flask to initiate the reaction. The remainder of the reagent mixture was then added to the reaction flask at a rate that would maintain a reaction temperature of between about 45° and 50° C.

After the addition of the remaining reagent mixture was completed, the contents of the reaction flask were heated to 90° C. for two hours, cooled to room temperature, and acidified with a 5 weight percent aqueous hydrochloric acid solution. The aqueous and organic layers were separated and the aqueous layer was washed with 100 mL of toluene. The organic layers were combined and dried over magnesium sulfate. The solvent, toluene, was removed under vacuum. The resulting residue was dissolved in diethyl ether and extracted with three 150 mL portions of a 5 weight percent aqueous sodium bicarbonate solution. The aqueous fractions were combined, acidified to a pH of 2, and extracted twice with diethyl ether. The organic fractions were combined and dried over magnesium sulfate. The solvent, diethyl ether, was removed under vacuum to yield 10 grams of a mixture of half-esters, 3-methoxycarbonyl-4-(1-naphthyl)-cis/trans-3-pentenoic acids.

STEP 2

The mixture of half esters from Step 1 (10.0 grams) and sodium acetate (10 grams) were added to a reaction flask containing 200 mL of acetic anhydride. The reaction mixture was refluxed for three hours, The acetic acid by-product and the unreacted acetic anhydride were removed under vacuum and the resulting residue was dissolved in methylene chloride and washed with water. The organic layer was separated, washed with a 5 weight percent aqueous sodium bicarbonate solution to remove base solubles, and dried over magnesium sulfate. The solvent, methylene chloride, was removed under vacuum to yield 10.0 grams of crude oil containing 1-acetoxy-3-methoxycarbonyl-4-methylphenanthrene.

STEP 3

The crude oil from Step 2 (10.0 grams) and 5 drops of concentrated hydrochloric acid were added to a reaction flask containing 200 mL of methanol. The reaction mixture was refluxed for several hours. The methanol was removed under vacuum and 2 grams of crystalline product, 1-hydroxy-3-methoxycarbonyl-4-methylphenanthrene, was collected by vacuum filtration.

STEP 4

1-Hydroxy-3-methoxycarbonyl-4-methylphenanthrene (2 grams, 0.0075 mole) from Step 3 and 1,1-diphenyl-2-propyn-1-ol (4.2 grams of a 37 weight percent solution in toluene) were added to a reaction flask containing 200 mL of toluene. The reaction mixture was heated to 37° C. A catalytic amount of dodecylbenzenesulfonic acid, an amount sufficient to produce a persistent deep red color, was added and the reaction mixture was stirred for three hours. Water was added to the reaction mixture and the resulting layers were separated. The aqueous layer was extracted once with toluene. The organic layers were combined and dried over magnesium sulfate. The solvent, toluene, was removed under vacuum. The crude product was chromatographed on silica gel twice, first using a 1:1 ethyl acetate:hexane eluant and then a chloroform eluant. The recovered product, 0.5 gram, had a nuclear magnetic resonance (NMR) spectrum which showed the product to have a structure consistent with 3,3-diphenyl-12-methoxycarbonyl-11-methyl-3H-phenanthro[1,2-b]pyran.

EXAMPLE 2

STEP 1

2'-Acetonaphthone (50 grams, 0.29 mole) and dimethyl succinate (46.8 grams, 0.32 mole) were added to an addition funnel and diluted to 300 mL with toluene. About 20 weight percent of the mixture was added slowly to a reaction flask containing 100 mL of toluene and sodium hydride (14.0 grams of a 60 weight percent suspension in mineral oil, 0.35 mole). One mL of methanol was added to the reaction flask to initiate the reaction. The remainder of the reagent mixture was then added to the reaction flask at a rate which would maintain a reaction temperature of between about 45° to 50° C. The reaction mixture was stirred at room temperature overnight and quenched with dilute aqueous acetic acid. The aqueous and organic layers were separated and the organic layer was washed with two 250 mL portions of 5 weight percent aqueous sodium bicarbonate solution. The resulting aqueous layers were combined and carefully acidified with concentrated hydrochloric acid and extracted with three 100 mL portions of methylene chloride. The organic extracts were combined and dried over magnesium sulfate. The solvent, methylene chloride, was removed under vacuum to yield 80 grams of a mixture of half-esters, 3-methoxycarbonyl-4-(2-naphthyl)-cis/trans-3-pentenoic acids.

STEP 2

The mixture of half-esters from Step 1 (80 grams) and sodium acetate (60 grams) were added to a reaction flask containing 250 mL of acetic anhydride, The reaction mixture was refluxed for three hours. The acetic acid by-product and the unreacted acetic anhydride were removed under vacuum and the resulting residue was dissolved in methylene chloride and washed with water. The resulting organic layer was washed with a 5 weight percent aqueous sodium bicarbonate solution and dried over magnesium sulfate. The solvent, methylene chloride, was removed under vacuum. The desired product was crystallized from methanol, vacuum filtered, and washed with a small amount of acetonitrile to yield 20.0 grams of 4-acetoxy-2-methoxycarbonyl-1-methylphenanthrene.

STEP 3

4-Acetoxy-2-methoxycarbonyl-1-methylphenanthrene (20.0 grams, 0.065 mole) from step 2 was added to a reaction flask containing one mL of concentrated hydrochloric acid in 300 mL of methanol. The reaction mixture was refluxed for three and one half hours. The methanol was removed under vacuum. The resulting crude crystalline product was washed with a small amount of acetonitrile and collected by vacuum filtration to yield 15.0 grams of the desired product, 4-hydroxy-2-methoxycarbonyl-1-methylphenanthrene.

STEP 4

4-Hydroxy-2-methoxycarbonyl-1-methylphenanthrene (1.0 gram, 0.0038 mole) from Step 3 and 1,1-diphenyl-2-propyn-1-ol (0.8 gram of a 37 weight percent solution in toluene) were added to a reaction flask containing 150 mL of toluene. The reaction mixture was heated to 35° C. A catalytic amount of dodecylbenzenesulfonic acid, an amount sufficient to produce a persistent deep red color, was added to the reaction and the reaction mixture was stirred for three hours. Water was added to the reaction mixture and the resulting layers were separated. The aqueous layer was extracted once with toluene. The organic layers were combined and dried over magnesium sulfate. The solvent, toluene, was removed under vacuum. The resulting residue was crystallized from a mixture of hexane/ether, washed with acetonitrile, and collected by vacuum filtration. The recovered product, about 0.7 gram, had a melting point of 197°–199° C. A NMR spectrum showed the product to have a structure consistent with 2,2-diphenyl-5-methoxycarbonyl-6-methyl-2H-phenanthro[4,3 -b]pyran.

EXAMPLE 3

The process of Example 2 was followed except that in Step 4, 1-(4-methoxyphenyl)-1-phenyl-2-propyn-1-ol (1.4 grams, 0.006 mole) was used in place of the 1,1-diphenyl-2-propyn-1-ol. The recovered product, about 1.3 grams, had a melting point of 160°–162° C. A NMR spectrum showed the product to have a structure consistent with 2-(4-methoxyphenyl)-2-phenyl-5-methoxycarbonyl-6-methyl-2H-phenanthro[ 4,3-b]pyran.

EXAMPLE 4

The process of Example 2 was followed except that in Step 1, 4-methoxy-1-naphthaldehyde (50.0 grams, 0.27 mole) was used in place of the 2'-acetonaphthone to produce 48.5 grams of a mixture of half-esters, 3-methoxycarbonyl-4-(4-methoxy-1-naphthyl)-cis/trans-3-butenoic acids. This mixture of half-esters (48.5 grams) was used in Step 2, and the reaction mixture was refluxed for one half hour instead of three hours to produce 32.0 grams of 1-acetoxy-3-methoxycarbonyl-9-methoxyphenanthrene. The intermediate, 1-acetoxy-3-methoxycarbonyl-9-methoxyphenanthrene (32.0 grams, 0.1 mole), was used in Step 3 to produce 20.0 grams of 1-hydroxy-3-methoxycarbonyl-9-methoxyphenanthrene, of which (5.0 grams, 0.0185 mole) was used in Step 4 with 1-(2-fluorophenyl)-1-(4-methoxyphenyl)-2-propyn-1-ol (4.7 grams, 0.0185 mole). The recovered product, about 2.5 grams, had a melting point of 214°–216° C. A NMR spectrum showed the product to have a structure consistent with 3-(2-fluorophenyl)-3-(4-methoxyphenyl)-6-methoxy-12-methoxycarbonyl-3H -phenanthro[1,2-b]pyran.

EXAMPLE 5

The process of Example 4 was followed except that in Step 4, 9-ethinyl-9-hydroxyfluorene(4.7 grams, 0.007 mole) was used in place of the 1-(2-fluorophenyl)-1-(4-methoxyphenyl)-2-propyn-1-ol, and the crude product was chromatographed on a silica gel column using ethyl acetate/hexane as the eluant. The recovered product, about 0.5 gram, had a melting point of 196°–199° C. A NMR spectrum showed the product to have a structure consistent with spiro[3H-6-methoxy-12-methoxycarbonylphenanthro[1,2-b]pyran-3-9' -fluorene].

EXAMPLE 6

The process of Example 2 was followed except that in Step 1, 6-methoxy-2-acetonaphthone (67.5 grams, 0.34 mole) was used in place of the 2'-acetonaphthone to produce 89.0 grams of a mixture of half-esters, 3-methoxycarbonyl-4-(6-methoxy-2-naphthyl)-cis/trans-3-pentenoic acids. This mixture of half-esters (89.0 grams) was used in Step 2, and the reaction mixture was refluxed for four hours instead of three hours to produce 21.0 grams of 4-acetoxy-7-methoxy-2-methoxycarbonyl-1-methylphenanthrene. This intermediate (21.0 grams, 0.065 mole) was used in Step 3, and the reaction mixture was refluxed for two hours instead of three and one half hours to produce 11.0 grams of 4-hydroxy-7-methoxy-2-methoxycarbonyl-1-methylphenanthrene, which product (1.5 grams, 0.0153 mole) was used in Step 4 with 1,1-bis(4-methoxyphenyl)-2-propyn-1-ol (1.4 grams, 0.0053 mole). The reaction mixture was stirred for one hour instead of three hours. The recovered product, about 1.8 grams, had a melting point of 214°–216° C. A NMR spectrum showed the product to have a structure consistent with 2,2-di(4-methoxyphenyl)-10-methoxy-5-methoxycarbonyl-6-methyl-2H-phenanthro[4,3-b]pyran.

EXAMPLE 7

STEP 1

1-Methoxynaphthalene (50.0 grams, 0.32 moles) and acetyl chloride (27.5 grams, 0.35 moles) were carefully added with stirring to a reaction flask containing a solution of aluminum chloride (51.0 grams, 0.38 moles) in 200 mL of methylene chloride. After stirring for 1 hour at room temperature the reaction mixture was poured over ice and stirred until colorless. The organic layer was separated, washed once with 200 mL of distilled water, and dried over sodium sulfate. The solvent, methylene chloride, was removed under vacuum. The product was crystallized using a mixture of hexane/diethyl ether and collected by vacuum filtration. The recovered product, about 49.0 grams, had a NMR spectrum which showed the product to have a structure consistent with 4-methoxy-1-acetonaphthone.

STEP 2

4-Methoxy-1-acetonaphthone (48.0 grams, 0.24 mole) from Step 1 and dimethyl succinate (38.0 grams, 0.26 mole) were added to a volumetric addition funnel. Toluene was added to the addition funnel to yield 200 mL of a reagent mixture. The reagent mixture was slowly added to a reaction flask containing a solution of potassium t-butoxide (29.2 grams, 0.26 mole) in 200 mL of toluene. The reaction mixture was heated to 75° C. and stirred for 3 hours. The reaction mixture was cooled and water was added to quench the reaction. The organic layer was separated and washed with water. The aqueous layers were combined and carefully acidified with concentrated hydrochloric acid to a pH of 2 and extracted with three 100 mL portions of methylene chloride. The organic extracts were combined and dried over magnesium sulfate. The solvent, methylene chloride, was removed under vacuum to yield 74 grams of a mixture of half-esters, 3-methoxycarbonyl-4-(methoxy-1-naphthyl)-cis/trans-3-pentenoic acids.

STEP 3

The mixture of half-esters from Step 2 (74.0 grams) and sodium acetate (30 grams) were added to a reaction flask containing 250 mL of acetic anhydride. The reaction mixture was refluxed for 6 hours. The acetic acid by-product and the unreacted acetic anhydride were removed under vacuum and the resulting residue was dissolved in methylene chloride and washed with water. The organic layer was separated, washed with a 5 weight percent sodium bicarbonate solution, and dried over magnesium sulfate. The solvent, methylene chloride, was removed under vacuum to yield 77 grams of crude oil containing 1-acetoxy-9-methoxy-3-methoxycarbonyl-4-methylphenanthrene.

STEP 4

The oil from Step 3 containing 1-acetoxy-9-methoxy-3-methoxycarbonyl-4-methylphenanthrene (77.0 grams, 0.236 mole) was added to a reaction flask containing one mL of concentrated hydrochloric acid in 300 mL of methanol. The reaction mixture was refluxed for 3 hours. The methanol was removed under vacuum and the crude product was purified on a silica gel column using a 1:4 ratio of ethyl acetate:hexane as the eluant. The product was crystallized from methanol and collected by vacuum filtration to yield 15.0 grams of 1-hydroxy-9-methoxy-3-methoxycarbonyl-4-methylphenanthrene.

STEP 5

1-Hydroxy-9-methoxy-3-methoxycarbonyl-4-methylphenanthrene (1.5 grams, 0.005 mole) from Step 4 and 1-(2,3-dihydrobenzofur-5-yl)-1-(4-methoxyphenyl)- 2-propyn-1-ol (1.4 grams, 0.005 mole) were added to a reaction flask containing 250 mL of toluene. The reaction mixture was heated to 35° C. A catalytic amount of dodecylbenzenesulfonic acid, an amount sufficient to produce a persistent deep red color, was added to the reaction and the reaction mixture stirred for one hour. Water was added to the reaction mixture and the resulting layers were separated. The aqueous layer was extracted once with toluene. The organic layers were combined and dried over magnesium sulfate. The solvent, toluene, was removed under vacuum. The crude product was crystallized from a mixture of hexane/ether and collected by vacuum filtration. The recovered product, about 1.0 gram, had a melting point of 143°–145° C. A NMR spectrum showed the product to have a structure consistent with 3-(2,3-dihydrobenzofur-5-yl)-3-(4-methoxyphenyl)-6-methoxy-12 -methoxycarbonyl-11-methyl-3H-phenanthro [1,2-b]pyran.

EXAMPLE 8

The process of Example 7 was followed except that in Step 1, benzoyl chloride (45.0 grams, 0.32 moles) was used in place of the acetyl chloride and the reaction was poured over ice after two hours instead of one hour to produce about 72.0 grams of 1-benzoyl-4-methoxynaphthalene; in Step 2, 1-benzoyl-4-methoxynaphthalene (72.0 grams, 0.28 mole) was used in place of the 4-methoxy-1-acetonaphthone and after the reaction mixture was heated to 75° C., it was maintained at that temperature for 12 hours and then stirred at room temperature for 24 hours to produce 83 grams of a mixture of half-esters, 3-methoxycarbonyl-4-(4-methoxy-1-naphthyl)-4-phenyl-cis/trans-3-butenoic acids; in Step 3, this mixture of half-esters (83.0 grams) was used and the reaction mixture was refluxed for three hours instead of six hours to produce 40 grams of a crude oil containing 1-acetoxy-9-methoxy-3-methoxycarbonyl-4-phenylphenanthrene, which was not purified further but used directly in the next step; in Step 4, the crude oil containing 1-acetoxy-9-methoxy-3-methoxycarbonyl-4-phenylphenanthrene (40 grams, 0.236 mole) was used to produce 7.5 grams of 1-hydroxy-9-methoxy-3-methoxycarbonyl-4 -phenylphenanthrene; and in Step 5, this intermediate, 1-hydroxy-9-methoxy-3-methoxycarbonyl-4-phenylphenanthrene (1.0 gram, 0.002 mole) was used with 1,1-diphenyl-2-propyn-1-ol (0.4 gram, 0.002 mole). The recovered product, about 0.5 gram, had a melting point of 185°–187° C. A NMR spectrum showed the product to have a structure consistent with 3,3-diphenyl-6-methoxy-12-methoxycarbonyl-11-phenyl-3H-phenanthro[1,2-b]pyran.

EXAMPLE 9

The process of Example 8 was followed except that in Step 5, 2-(2-methyl-2,3-dihydrobenzofur-5-yl)-2-(4-methoxyphenyl)-2-propyn-1-ol (2.5 grams, 0.008 mole) was used in place of the 1,1-diphenyl-2-propyn-1-ol, the reaction mixture was stirred for three hours instead of one hour, and the crude product was chromatographed on a silica gel column using a 1:1 mixture of ethyl acetate:hexane as the eluant. The recovered product, about 1.5 grams, had a melting point of 209°–211° C. A NMR spectrum showed the product to have a structure consistent with 3-(4-methoxyphenyl)-3-(2-methyl-2,3-dihydrobenzofur-5-yl)-6-methoxy- 12-methoxycarbonyl-11-phenyl-3H-phenanthro[1,2-b]pyran.

EXAMPLE 10

3-(4-methoxyphenyl)-3-(2-methyl-2,3-dihydrobenzofur-5-yl)-6-methoxy-12-methoxycarbonyl- 11-phenyl-3H-phenanthro[1,2-b]pyran (1.0 gram, 0.002 mole) prepared in Example 9 was added to a reaction flask containing 100 mL of tetrahydrofuran and stirred until dissolved. Lithium aluminum hydride (0.2 grams, 0,005 mole) was added slowly to the reaction flask with stirring. The reaction mixture was refluxed for one hour. After cooling, 2-propanol was added slowly to quench the reaction. The reaction mixture was acidified by the addition of 5 weight percent aqueous hydrochloric acid. The resulting mixture was extracted with three 100 mL portions of diethyl ether. The extracts were combined and dried over magnesium sulfate. The solvent, diethyl ether, was removed under vacuum. The product was crystallized from diethyl ether and collected by vacuum filtration. A NMR spectrum of the recovered product, 0.3 gram, showed the product to have a structure consistent with 3-(4-methoxyphenyl)-3-(2-methyl-2,3-dihydrobenzofur-5-yl)-6-methoxy-12-hydroxymethyl-11 -phenyl-3H-phenanthro[1,2-b]pyran.

EXAMPLE 11

The principal products of the Example Compounds were dissolved in diethylene glycol dimethyl ether. The concentration of the resulting solutions was approximately 0.5 milligram per milliliter. Each solution was tested in a UV spectrophotometer to determine the two wavelengths in the ultraviolet range closest to the visible spectrum or in the threshold range, i.e., 390 to 410 nanometers, of the visible spectrum, at which the absorption of the photochromic compound occurs. These results are reported as the Ultraviolet Absorption Wavelengths in Table 1.

The Visible Absorption Wavelengths reported in Table 1 were determined by testing prepared photochromic test square polymerizates imbibed with the principal products of the Example Compounds. The test square polymerizates were prepared from a diethylene glycol bis(allyl carbonate) composition and measured ⅛" (0.3 centimeters) ×2" (5.1 centimeters)×2" (5.1 centimeters). The photochromic phenanthropyrans were dissolved to form a 10 weight percent solution in a 1:9 mixture of ethyl cellulose:toluene. The solution was then spin coated onto the test squares and allowed to dry. Samples were then heated in a hot-air oven at 35°–155° C. for a period of time sufficient to thermally transfer the photochromic into the test squares. After cooling, the ethyl cellulose/toluene resin film was removed from the test squares by washing with acetone. The photochromic squares were tested for visible absorption wavelength in a UV spectrophotometer.

TABLE 1

| COMPOUND EXAMPLE | ULTRAVIOLET ABSORPTION WAVELENGTHS | VISIBLE ABSORPTION WAVELENGTHS |
|---|---|---|
| 1 | 369/388 nm | 431/506 nm |
| 2 | 365/384 nm | 448/490 nm |
| 3 | 365/384 nm | 463/517 nm |
| 4 | 375/395 nm | 462/539 nm |
| 5 | 379/399 nm | 439/553 nm |
| 6 | 369/389 nm | 466/537 nm |
| 7 | 376/396 nm | 472/568 nm |
| 8 | 374/393 nm | 426/550 nm |
| 9 | 374/393 nm | 475/577 nm |

The results in Table 1 reveal that the Compound Examples in solution and in the test polymerizates become activated and change light transmission properties when subjected to ultraviolet radiation. After removal of the ultraviolet light source, the color of each of the solutions and test polymerizates containing the Compound Examples reverted to their original color or colorless state. These findings demonstrate the photochromic properties of the Compound Examples.

The present invention has been described with reference to specific details of particular embodiments thereof, it is not intended that such details be regarded as limitations upon the scope of the invention except insofar as to the extent that they are included in the accompanying claims.

I claim:

1. A phenanthropyran compound represented by one of the following graphic formulae:

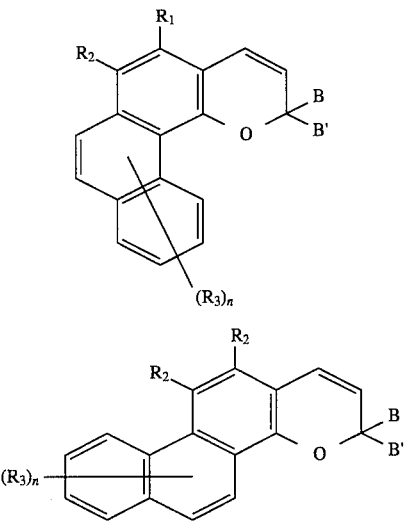

wherein,
(a) $R_1$ is the group, —$CH_2X$ or —C(O)Y, wherein X is hydroxy, benzoyloxy, $C_1$–$C_6$ alkoxy, $C_1$–$C_6$ acyloxy, $C_2$–$C_6$ dialkylamino, or trimethylsilyloxy, Y is the group, —$OR_4$ or —N($R_5$)$R_6$, wherein $R_4$ is hydrogen, $C_1$–$C_6$ alkyl, phenyl, mono ($C_1$–$C_6$) alkyl substituted phenyl, mono ($C_1$–$C_6$) alkoxy substituted phenyl, phenyl($C_1$–$C_3$)alkyl, mono($C_1$–$C_6$)alkyl substituted phenyl ($C_1$–$C_3$ ) alkyl, mono ($C_1$–$C_6$ ) alkoxy substituted phenyl ($C_1$–$C_3$) alkyl, $C_1$–$C_6$ alkoxy($C_2$–$C_4$)alkyl, or $C_1$–$C_6$ haloalkyl, $R_5$ and $R_6$ are each selected from the group consisting of hydrogen, $C_1$–$C_6$ alkyl, $C_5$–$C_7$ cycloalkyl, phenyl, mono-substituted phenyl, and di-substituted phenyl, or $R_5$ and $R_6$ together with the nitrogen atom form an unsubstituted, mono-substituted, or di-substituted heterocyclic ring containing from 5 to 6 ring atoms, which heterocyclic ring has said nitrogen atom as the sole hetero atom, said phenyl and heterocyclic ring substituents being $C_1$–$C_6$ alkyl or $C_1$–$C_6$ alkoxy, said halo substituent being chloro or fluoro;

(b) $R_2$ is hydrogen, $C_1$–$C_6$ alkyl, $C_3$–$C_7$ cycloalkyl, pyridyl, phenyl, mono-substituted or di-substituted phenyl, said phenyl substituents being $C_1$–$C_6$ alkyl, $C_1$–$C_6$ alkoxy, chloro, or fluoro;

(c) each $R_3$ is chloro, fluoro, amino, $C_1$–$C_6$ monoalkylamino, $C_2$–$C_6$ dialkylamino, $C_1$–$C_6$ alkyl, or -$OR_7$, wherein $R_7$ is hydrogen, $C_1$–$C_6$ alkyl, allyl, or acetyl, and n is the integer 0, 1, or 2; and (d) B and B' are each selected from the group consisting of:

(i) the unsubstituted, and the mono-, di-, or tri-substituted aryl groups phenyl and naphthyl;

(ii) the substituted or unsubstituted heterocyclic aromatic groups pyridyl, furanyl, benzofuranyl, thienyl, and benzothienyl, said aryl and heterocyclic substituents being selected from the group consisting of hydroxy, amino, $C_1$–$C_6$ monoalkylamino, $C_2$–$C_6$ dialkylamino, $C_1$–$C_6$ alkyl, $C_1$–$C_6$ haloalkyl, $C_1$–$C_6$ alkoxy, mono($C_1$–$C_6$)alkoxy($C_1$–$C_4$)alkyl, acryloxy, methacryloxy, and halogen, said halogen or (halo) group being fluoro or chloro;

(iii) the groups represented by the following graphic formulae:

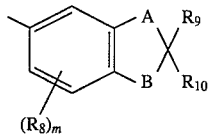 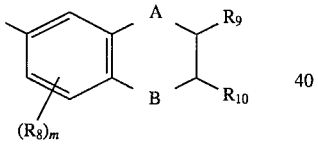

wherein A is carbon or oxygen and B is oxygen or substituted nitrogen, provided that when B is substituted nitrogen, A is carbon, said nitrogen substituents being selected from the group consisting of hydrogen, $C_1$–$C_6$ alkyl, and $C_2$–$C_6$ acyl; each $R_8$ is $C_1$–$C_6$ alkyl, $C_1$–$C_6$ alkoxy, hydroxy, or halogen, said halogen being chloro or fluoro; $R_9$ and $R_{10}$ are each hydrogen or $C_1$–$C_6$ alkyl; and m is the integer 0, 1, or 2; and (iv) $C_1$–$C_6$ alkyl, $C_1$–$C_6$ haloalkyl, $C_1$–$C_6$ alkoxy($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl($C_3$–$C_6$)cycloalkyl, and halo($C_3$–$C_6$)cycloalkyl, said halo group being fluoro or chloro; and (v) B and B' taken together form a substituted or unsubstituted fluoren-9-ylidene or a substituted or unsubstituted, saturated bicyclic ring selected from the group consisting of adamantylidene, bornylidene, norbornylidene, and bicyclo(3.3.1)nonan-9-ylidene.

2. The phenanthropyran compound of claim 1 represented by one of the following graphic formulae:

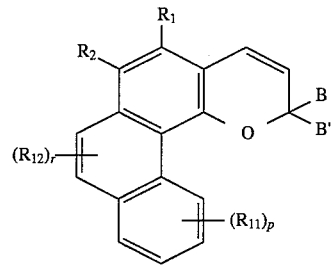

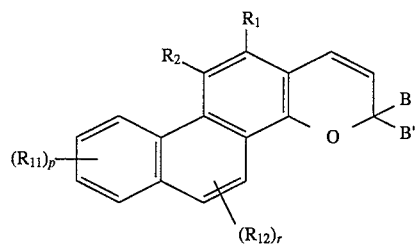

wherein, (a) X in the group —$CH_2X$ is hydroxy, $C_1$–$C_4$ alkoxy, $C_1$–$C_4$ acyloxy, or $C_2$–$C_4$ dialkylamino, $R_4$ in the group —$OR_4$ is hydrogen, $C_1$–$C_4$ alkyl, phenyl, mono ($C_1$–$C_4$) alkyl substituted phenyl, mono ($C_1$–$C_4$) alkoxy substituted phenyl, phenyl ($C_1$–$C_2$) alkyl, mono ($C_1$–$C_4$) alkyl substituted phenyl ($C_1$–$C_2$) alkyl, mono ($C_1$–$C_4$) alkoxy substituted phenyl($C_1$–$C_2$)alkyl, $C_1$–$C_4$ alkoxy($C_2$–$C_3$)alkyl, or $C_1$–$C_4$ haloalkyl, $R_5$ and $R_6$ in the group —$N(R_5)$ $R_6$ are each selected from the group consisting of hydrogen, $C_1$–$C_4$ alkyl, $C_5$–$C_6$ cycloalkyl, phenyl, mono-substituted phenyl, and di-substituted phenyl, said phenyl substituents being $C_1$–$C_4$ alkyl or $C_1$–$C_4$ alkoxy, said halo substituent being chloro or fluoro;

(b) $R_2$ is hydrogen, $C_1$–$C_4$ alkyl, $C_3$–$C_5$ cycloalkyl, phenyl, mono-substituted phenyl, or di-substituted phenyl, said phenyl substituents being $C_1$–$C_4$ alkyl, $C_1$–$C_4$ alkoxy, chloro, or fluoro;

(c) $R_{11}$ and $R_{12}$ are each selected from the group consisting of chloro, fluoro, amino, $C_1$–$C_6$ monoalkylamino, $C_2$–$C_6$ dialkylamino, $C_1$–$C_4$ alkyl, and —$OR_7$ wherein $R_7$ is hydrogen, $C_1$–$C_4$ alkyl, or acetyl, and p and r are each the integers 0 or 1; and (d) B and B' are each selected from the group consisting of:

(i) phenyl, mono-substituted phenyl, or di-substituted phenyl; said phenyl substituents being $C_1$–$C_3$ alkyl, $C_1$–$C_3$ alkoxy, amino, $C_1$–$C_4$ monoalkylamino, $C_2$–$C_4$ dialkylamino, or fluoro;

(ii) the groups represented by the following graphic formulae:

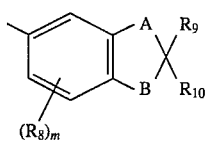 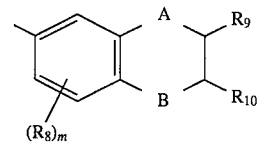

wherein A is carbon and B is oxygen, $R_8$ is $C_1$–$C_3$ alkyl or $C_1$–$C_3$ alkoxy, and $R_9$ and $R_{10}$ are each hydrogen or $C_1$–$C_4$ alkyl; and m is the integer 0 or 1; and (iii) $C_1$–$C_4$ alkyl; and (iv) B and B' taken together form substituted or unsubstituted fluoren-9-ylidene or adamantylidene.

3. The phenanthropyran compound of claim 2 wherein,
(a) X in the group —CH$_2$X is hydroxy, C$_1$–C$_3$ alkoxy, or C$_1$–C$_3$ acyloxy; R$_4$ in the group —OR$_4$ is hydrogen, C$_1$–C$_3$ alkyl, or phenyl, and R$_5$ and R$_6$ in the group —N(R$_5$)R$_6$ are each hydrogen or C$_1$–C$_3$ alkyl;
(b) R$_2$ is hydrogen, C$_1$–C$_3$ alkyl, phenyl, or monosubstituted phenyl, said phenyl substituents being C$_1$–C$_2$ alkyl, C$_1$–C$_2$ alkoxy, or fluoro; and
(c) R$_{11}$ and R$_{12}$ are each C$_1$–C$_3$ alkyl or —OR$_7$, wherein R$_7$ is hydrogen, C$_1$–C$_3$ alkyl, or acetyl.

4. A phenanthropyran compound selected from the group consisting of:
(a) 3,3-diphenyl-12-methoxycarbonyl-11-methyl-3H-phenanthro[1,2-b]pyran;
(b) 2,2-diphenyl-5-methoxycarbonyl-6-methyl-2H-phenanthro[4,3-b]pyran;
(c) 2-(4-methoxyphenyl)-2-phenyl-5-methoxycarbonyl-6-methyl-2H-phenanthro[4,3-b]pyran;
(d) 3-(2-fluorophenyl)-3-(4-methoxyphenyl)-6-methoxy-12-methoxycarbonyl-3H-phenanthro[1,2 -b]pyran;
(e) spiro [3H-6-methoxy-12-methoxycarbonylphenanthro[1,2-b]pyran-3-9'-fluorene];
(f) 2,2-di(4-methoxyphenyl)-10-methoxy-5-methoxycarbonyl-6-methyl-2H-phenanthro[4,3-b]pyran;
(g) 3-(2,3-dihydrobenzofur-5-yl)-3-(4-methoxyphenyl)-6-methoxy-12-methoxycarbonyl-11-methy -3H-phenanthro[1,2-b]pyran;
(h) 3,3-diphenyl-6-methoxy-12-methoxycarbonyl-11-phenyl-3H-phenanthro[1,2-b]pyran;
(i) 3-(4-methoxyphenyl)-3-(2-methyl-2,3-dihydrobenzofur-5-yl)-6-methoxy-12-methoxycarbonyl -11-phenyl-3H-phenanthro[1,2-b]pyran;
(j) 3-(4-methoxyphenyl)-3-(2-methyl-2,3-dihydrobenzofur-5-yl)-6-methoxy-12-hydroxymethyl -11-phenyl-3H-phenanthro[1,2-b]pyran; and
(k) 2,2-diphenyl-5-N,N-dimethylaminocarbonyl-2H-phenanthro[4,3-b]pyran.

5. A photochromic article comprising a polymeric organic host material and a photochromic amount of a phenanthropyran compound represented by one of the following graphic formulae:

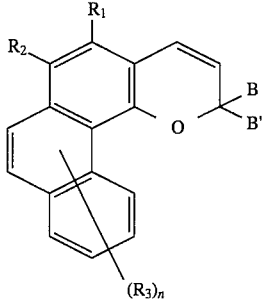

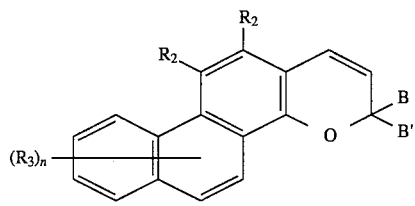

wherein,
(a) R$_1$ is the group, —CH$_2$X or —C(O)Y, wherein X is hydroxy, benzoyloxy, C$_1$–C$_6$ alkoxy, C$_1$–C$_6$ acyloxy, C$_2$–C$_6$ dialkylamino, or trimethylsilyloxy, Y is the group, —OR$_4$ or —N(R$_5$)R$_6$, wherein R$_4$ is hydrogen, C$_1$–C$_6$ alkyl, phenyl, mono(C$_1$–C$_6$)alkyl substituted phenyl, mono (C$_1$–C$_6$) alkoxy substituted phenyl, phenyl (C$_1$–C$_3$) alkyl, mono (C$_1$–C$_6$) alkyl substituted phenyl (C$_1$–C$_3$) alkyl, mono (C$_1$–C$_6$) alkoxy substituted phenyl (C$_1$–C$_3$) alkyl, C$_1$–C$_6$ alkoxy(C$_2$–C$_4$) alkyl, or C$_1$–C$_6$ haloalkyl, R$_5$ and R$_6$ are each selected from the group consisting of hydrogen, C$_1$–C$_6$ alkyl, C$_5$–C$_7$ cycloalkyl, phenyl, mono-substituted phenyl, and di-substituted phenyl, or R$_5$ and R$_6$ together with the nitrogen atom form an unsubstituted, mono-substituted, or di-substituted heterocyclic ring containing from 5 to 6 ring atoms, which heterocyclic ring has said nitrogen atom as the sole hetero atom, said phenyl and heterocyclic ring substituents being C$_1$–C$_6$ alkyl or C$_1$–C$_6$ alkoxy, said halo substituent being chloro or fluoro;
(b) R$_2$ is hydrogen, C$_1$–C$_6$ alkyl, C$_3$–C$_7$ cycloalkyl, pyridyl, phenyl, mono-substituted or di-substituted phenyl, said phenyl substituents being C$_1$–C$_6$ alkyl, C$_1$–C$_6$ alkoxy, chloro, or fluoro;
(c) each R$_3$ is chloro, fluoro, amino, C$_1$–C$_6$ monoalkylamino, C$_2$–C$_6$ dialkylamino, C$_1$–C$_6$ alkyl, or —OR$_7$, wherein R$_7$ is hydrogen, C$_1$–C$_6$ alkyl, allyl, or acetyl, and n is the integer 0, 1, or 2; and
(d) B and B' are each selected from the group consisting of:
(i) the unsubstituted, and the mono-, di-, or tri-substituted aryl groups phenyl and naphthyl;
(ii) the substituted or unsubstituted heterocyclic aromatic groups pyridyl, furanyl, benzofuranyl, thienyl, and benzothienyl, said aryl and heterocyclic substituents being selected from the group consisting of hydroxy, amino, C$_1$–C$_6$ monoalkylamino, C$_2$–C$_6$ dialkylamino, C$_1$–C$_6$ alkyl, C$_1$–C$_6$ haloalkyl, C$_1$–C$_6$ alkoxy, mono(C$_1$–C$_6$)alkoxy(C$_1$–C$_4$)alkyl, acryloxy, methacryloxy, and halogen, said halogen or (halo) group being fluoro or chloro;
(iii) the groups represented by the following graphic formulae:

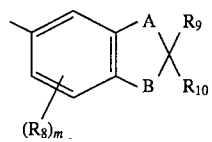 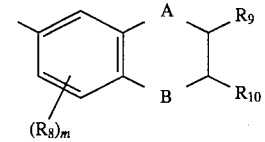

wherein A is carbon or oxygen and B is oxygen or substituted nitrogen, provided that when B is substituted nitrogen, A is carbon, said nitrogen substituents being selected from the group consisting of hydrogen, C$_1$–C$_6$ alkyl, and C$_2$–C$_6$ acyl; each R$_8$ is C$_1$–C$_6$ alkyl, C$_1$–C$_6$ alkoxy, hydroxy, or halogen, said halogen being chloro or fluoro; R$_9$ and R$_{10}$ are each hydrogen or C$_1$–C$_6$ alkyl; and m is the integer 0, 1, or 2; and
(iv) C$_1$–C$_6$ alkyl, C$_1$–C$_6$ haloalkyl, C$_1$–C$_6$ alkoxy(C$_1$–C$_4$)alkyl, C$_3$–C$_6$ cycloalkyl, mono(C$_1$–C$_6$) alkoxy(C$_3$–C$_6$)cycloalkyl, mono(C$_1$–C$_6$)alkyl(C$_3$–C$_6$)cycloalkyl, and halo(C$_3$–C$_6$)cycloalkyl, said halo group being fluoro or chloro; and
(v) B and B' taken together form a substituted or unsubstituted fluoren-9-ylidene or a substituted or unsubstituted, saturated bicyclic ring selected from the group consisting of adamantylidene, bornylidene, norbornylidene, and bicyclo(3.3.1)nonan-9-ylidene.

6. The photochromic article of claim 5 wherein the polymeric organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyurethane, poly(ethylene terephthalate), polystyrene, copoly (styrene-methylmethacrylate), copoly (styrene-acrylonitrile), polyvinylbutyral and polymers of members of the group consisting of polyol (allyl carbonate) monomers, polyfunctional acrylate monomers, and diallylidene pentaerythritol monomers.

7. The photochromic article of claim 6 wherein the phenanthropyran compound is represented by one of the following graphic formulae:

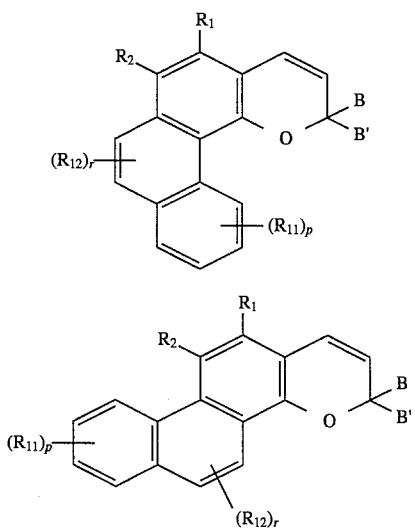

wherein,
(a) X in the group —CH$_2$X is hydroxy, C$_1$–C$_4$ alkoxy, C$_1$–C$_4$ acyloxy, or C$_2$–C$_4$ dialkylamino, R$_4$ in the group —OR$_4$ is hydrogen, C$_1$–C$_4$ alkyl, phenyl, mono(C$_1$–C$_4$)alkyl substituted phenyl, mono (C$_1$–C$_4$) alkoxy substituted phenyl, phenyl (C$_1$–C$_2$) alkyl, mono (C$_1$–C$_4$) alkyl substituted phenyl (C$_1$–C$_2$) alkyl, mono (C$_1$–C$_4$) alkoxy substituted phenyl(C$_1$–C$_2$)alkyl, C$_1$–C$_4$ alkoxy(C$_2$–C$_3$)alkyl, or C$_1$–C$_4$ haloalkyl, R$_5$ and R$_6$ in the group —N(R$_5$)R$_6$ are each selected from the group consisting of hydrogen, C$_1$–C$_4$ alkyl, C$_5$–C$_6$ cycloalkyl, phenyl, mono-substituted phenyl, and di-substituted phenyl, said phenyl substituents being C$_1$–C$_4$ alkyl or C$_1$–C$_4$ alkoxy, said halo substituent being chloro or fluoro;

(b) R$_2$ is hydrogen, C$_1$–C$_4$ alkyl, C$_3$–C$_5$ cycloalkyl, phenyl, mono-substituted phenyl, or di-substituted phenyl, said phenyl substituents being C$_1$–C$_4$ alkyl, C$_1$–C$_4$ alkoxy, chloro, or fluoro;

(c) R$_{11}$ and R$_{12}$ are each selected from the group consisting of chloro, fluoro, amino, C$_1$–C$_6$ monoalkylamino, C$_2$–C$_6$ dialkylamino, C$_1$–C$_4$ alkyl, and —OR$_7$ wherein R$_7$ is hydrogen, C$_1$–C$_4$ alkyl, or acetyl, and p and r are each the integers 0 or 1; and (d) B and B' are each selected from the group consisting of:
(i) phenyl, mono-substituted phenyl, or di-substituted phenyl; said phenyl substituents being C$_1$–C$_3$ alkyl, C$_1$–C$_3$ alkoxy, amino, C$_1$–C$_4$ monoalkylamino, C$_2$–C$_4$ dialkylamino, or fluoro;

(ii) the groups represented by the following graphic formulae:

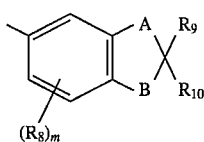 , 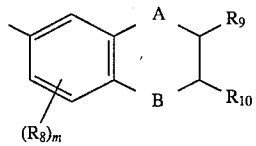

wherein A is carbon and B is oxygen, R$_8$ is C$_1$–C$_3$ alkyl or C$_1$–C$_3$ alkoxy, and R$_9$ and R$_{10}$ are each hydrogen or C$_1$–C$_4$ alkyl; and m is the integer 0 or 1; and
(iii) C$_1$–C$_4$ alkyl; and
(iv) B and B' taken together form substituted or unsubstituted fluoren-9-ylidene or adamantylidene.

8. The photochromic article of claim 7 wherein the phenanthropyran compound is one wherein,
(a) X in the group —CH$_2$X is hydroxy, C$_1$–C$_3$ alkoxy, or C$_1$–C$_3$ acyloxy; R$_4$ in the group —OR$_4$ is hydrogen, C$_1$–C$_3$ alkyl, or phenyl, and R$_5$ and R$_6$ in the group —N(R$_5$)R$_6$ are each hydrogen or C$_1$–C$_3$ alkyl;
(b) R$_2$ is hydrogen, C$_1$–C$_3$ alkyl, phenyl, or mono-substituted phenyl, said phenyl substituents being C$_1$–C$_2$ alkyl, C$_1$–C$_2$ alkoxy, or fluoro; and
(c) R$_{11}$ and R$_{12}$ are each C$_1$–C$_3$ alkyl or —OR$_7$, wherein R$_7$ is hydrogen, C$_1$–C$_3$ alkyl, or acetyl.

9. The photochromic article of claim 8 wherein the polymeric organic host material is a solid transparent homopolymer or copolymer of diethylene glycol bis(allyl carbonate), thermoplastic polycarbonate, poly(methylmethacrylate), polyvinylbutyral, or a polyurethane.

10. The photochromic article of claim 9 wherein the photochromic compound is present in an amount of from about 0.15 to 0.35 milligrams per square centimeter of organic host material surface to which the photochromic substance(s) is incorporated or applied.

11. The photochromic article of claim 10 wherein the article is a lens.

12. A photochromic article comprising, in combination, a solid transparent polymeric organic host material, and a photochromic amount of each of (a) a phenanthropyran compound of claim 1, and (b) different organic photochromic compound(s) having at least one activated absorption maxima within the range of between about 400 and 700 nanometers.

13. The photochromic article of claim 12 wherein the polymeric organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyurethane, poly(ethylene terephthalate), polystyrene, copoly(styrene-methylmethacrylate), copoly(styrene-acrylonitrile), polyvinylbutyral and polymers of members of the group consisting of polyol(allyl carbonate) monomers, polyfunctional acrylate monomers, and diallylidene pentaerythritol monomers.

14. The photochromic article of claim 13 wherein the organic photochromic compound (b) is selected from the group consisting of:
(a) a first organic photochromic substance having an activated absorption maxima in the visible range of greater than 590 nanometers;
(b) a second organic photochromic substance having at least one absorption maximum in the visible range of between 400 and less than 500 nanometers; and (c) a third organic photochromic substance having an absorption maximum within the visible range of between about 400 and 500 nanometers and an absorption maximum within the visible range of between 500 and 700 nanometers.

15. The photochromic article of claim 14 wherein the phenanthropyran compound is represented by one of the following graphic formulae:

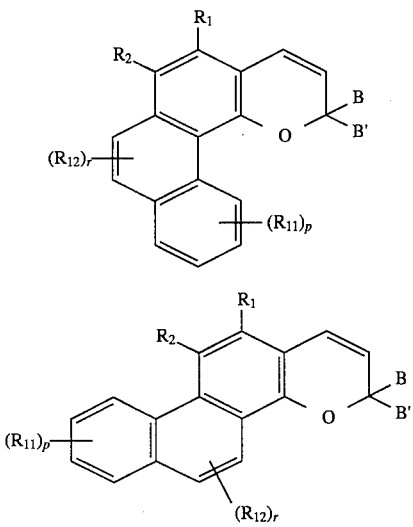

wherein, (a) $R_1$ is the group, —$CH_2X$ or —$C(O)Y$, wherein X is hydroxy, $C_1$–$C_4$ alkoxy, $C_1$–$C_4$ acyloxy, or $C_2$–$C_4$ dialkylamino, Y is the group, —$OR_4$ or —$N(R_5)R_6$, wherein $R_4$ is hydrogen, $C_1$–$C_4$ alkyl, phenyl, mono($C_1$–$C_4$)alkyl substituted phenyl, mono($C_1$–$C_4$)alkoxy substituted phenyl, phenyl ($C_1$–$C_2$) alkyl, mono ($C_1$–$C_4$) alkyl substituted phenyl ($C_1$–$C_2$) alkyl, mono ($C_1$–$C_4$) alkoxy substituted phenyl ($C_1$–$C_2$) alkyl, $C_1$–$C_4$ alkoxy($C_2$–$C_3$) alkyl, or $C_1$–$C_4$ haloalkyl, $R_5$ and $R_6$ are each selected from the group consisting of hydrogen, $C_1$–$C_4$ alkyl, $C_5$–$C_6$ cycloalkyl, phenyl, mono-substituted phenyl, and di-substituted phenyl, said phenyl substituents being $C_1$–$C_4$ alkyl or $C_1$–$C_4$ alkoxy, said halo substituent being chloro or fluoro;

(b) $R_2$ is hydrogen, $C_1$–$C_4$ alkyl, $C_3$–$C_5$ cycloalkyl, phenyl, mono-substituted phenyl, or di-substituted phenyl, said phenyl substituents being $C_1$–$C_4$ alkyl, $C_1$–$C_4$ alkoxy, chloro, or fluoro;

(c) $R_{11}$ and $R_{12}$ are each selected from the group consisting of chloro, fluoro, amino, $C_1$–$C_6$ monoalkylamino, $C_2$–$C_6$ dialkylamino, $C_1$–$C_4$ alkyl, and —$OR_7$ wherein $R_7$ is hydrogen, $C_1$–$C_4$ alkyl, or acetyl, and p and r are each the integers 0 or 1; and (d) B and B' are each selected from the group consisting of:

(i) phenyl, mono-substituted phenyl, or di-substituted phenyl; said phenyl substituents being $C_1$–$C_3$ alkyl, $C_1$–$C_3$ alkoxy, amino, $C_1$–$C_4$ monoalkylamino, $C_2$–$C_4$ dialkylamino, or fluoro;

(ii) the groups represented by the following graphic formulae:

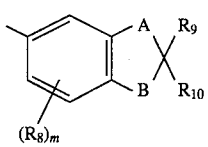 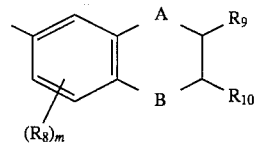

wherein A is carbon and B is oxygen, $R_8$ is $C_1$–$C_3$ alkyl or $C_1$–$C_3$ alkoxy, and $R_9$ and $R_{10}$ are each hydrogen or $C_1$–$C_4$ alkyl; and m is the integer 0 or 1;

(iii) $C_1$–$C_4$ alkyl; and (iv) B and B' taken together form substituted or unsubstituted fluoren-9-ylidene or adamantylidene.

16. The photochromic article of claim 15 wherein the polymeric organic host material is a solid transparent homopolymer or copolymer of diethylene glycol bis (allyl carbonate), thermoplastic polycarbonate, poly (methylmethacrylate), polyvinylbutyral, or a polyurethane.

17. The photochromic article of claim 16 wherein the organic photochromic compound (b) is selected from the group consisting of spiro(indoline)naphthoxazines, spiro(indoline)pyridobenzoxazines, spiro(benzindoline)pyridobenzoxazines, spiro(benzindoline)naphthoxazines, spiro(benzindoline)naphthopyrans, spiro(indoline)benzoxazines, spiro(indoline)benzopyrans, spiro(indoline)naphthopyrans, spiro(indoline)quinopyrans, spiro(indoline)pyrans, chromenes, and mixtures of such photochromic compounds.

18. The photochromic article of claim 17 wherein the phenanthropyran compound is one wherein, (a) X in the group —$CH_2X$ is hydroxy, $C_1$–$C_3$ alkoxy, or $C_1$–$C_3$ acyloxy; $R_4$ in the group —$OR_4$ is hydrogen, $C_1$–$C_3$ alkyl, or phenyl, and $R_5$ and $R_6$ in the group —$N(R_5)R_6$ are each hydrogen or $C_1$–$C_3$ alkyl;

(b) $R_2$ is hydrogen, $C_1$–$C_3$ alkyl, phenyl, or mono-substituted phenyl, said phenyl substituents being $C_1$–$C_2$ alkyl, $C_1$–$C_2$ alkoxy, or fluoro; and (c) $R_{11}$ and $R_{12}$ are each $C_1$–$C_3$ alkyl or —$OR_7$, wherein $R_7$ is hydrogen, $C_1$–$C_3$ alkyl, or acetyl.

19. The photochromic article of claim 18 wherein the photochromic compound is present in an amount of from about 0.15 to 0.35 milligrams per square centimeter of organic host material surface to which the photochromic substance(s) is incorporated or applied.

20. The photochromic article of claim 19 wherein the article is an ophthalmic lens.

* * * * *